United States Patent [19]

Bouillon et al.

[11] Patent Number: 5,830,445
[45] Date of Patent: Nov. 3, 1998

[54] ABRASIVE IN COSMETIC PRODUCTS, PROCESS FOR THEIR PRODUCTION AND USES THEREOF

[75] Inventors: Günter Bouillon, Kempen; Günter Daniel, Krefeld; Horst Denzer, Düsseldorf; Reinmar Peppmöller, Krefeld; Martin Franzen, Duisburg, all of Germany

[73] Assignee: Chemische Fabrik Stockhausen GmbH, Krefeld, Germany

[21] Appl. No.: 430,706

[22] Filed: Apr. 27, 1995

Related U.S. Application Data

[63] Continuation of Ser. No. 70,350, filed as PCT/EP91/02224, Nov. 26, 1991, abandoned.

[30] Foreign Application Priority Data

Nov. 29, 1990 [DE] Germany .......................... 40 38 076.9

[51] Int. Cl.⁶ ................................ A61K 7/48; A61K 7/50
[52] U.S. Cl. ........................ 424/69; 424/401; 424/195.1; 514/846
[58] Field of Search .................................. 424/74, 195.1, 424/401, 489, 69; 514/846

[56] References Cited

U.S. PATENT DOCUMENTS

| | | | |
|---|---|---|---|
| 2,561,043 | 7/1951 | Ayers | 241/31 |
| 2,622,047 | 3/1952 | Ayers | 134/7 |
| 4,557,854 | 12/1985 | Plueddemann | 252/174.15 |

OTHER PUBLICATIONS

*Research & Industry*, Bhaha et al "An improved technology for bleaching and washing offin shell walnuts" vol. 29 (1984) pp. 10–16. (Abstract Only).

*Primary Examiner*—Sally Gardner-Lane
*Attorney, Agent, or Firm*—Sprung Kramer Schaefer & Briscoe

[57] ABSTRACT

The present invention is directed to an abrasive for use in a skin cleansing agent. The abrasive comprises a bleached flour obtained from a natural shell, kernel or mixture thereof. A preferred bleaching agent is hydrogen peroxide. The natural shells and/or kernels may be, for example, walnut shells, almond shells, hazelnut shells, olive kernels, cherry kernels, apricot kernels or mixtures thereof.

26 Claims, No Drawings

ABRASIVE IN COSMETIC PRODUCTS, PROCESS FOR THEIR PRODUCTION AND USES THEREOF

This application is a continuation of application Ser. No. 08/070,350, filed on May 27, 1993 now abandoned and which claims a priority, filed as PCT/EP91/02224, Nov. 26, 1991 under 35 USC 371.

BACKGROUND OF THE INVENTION

The present invention relates to a finely divided material of natural shells and/or kernels treated with a bleaching agent, in particular hydrogen peroxide, and which is comprised in cosmetic products as an abrasive, to a process for the production thereof and to uses of the abrasive.

An important component of cosmetic cleansing agents and preparations is the abradant which has the function of mechanically supporting the cleaning action of detergent or surface-active components.

According to the state of the art, a variety of inorganic and organic materials may be used as mechanical cleaning agents and remedies in cleansing preparations, e.g., hand cleaning agents or so-called peeling creams and special cleaning gels for the removal of the uppermost, dead skin cells or diseased skin, e.g., of the face or other parts of the body.

EP-B-01 04 679 discloses an abrasive material consisting of agglomerates of finely divided grinding material agglomerated by means of an organic binder; calcite is used as abrasive. Several other abrasive materials are known, for example, chalk, marble, dolomite, feldspar, or quartz. Due to their strong abrasive action these materials are unsuitable for many applications. According to said patent, the calcite which is agglomerated in very fine distribution with a hydrophobic organic binder avoids scratching of sensitive surfaces.

The addition of a chlorine-forming bleach is mentioned in Example 4 wherein the chlorine supports the cleaning action of the abrasive and, if used to clean plastic surfaces, has a germicidal action.

U.S. Pat. No. 2,561,043 relates to a special device in which, amongst others, nutshell flours may be produced from nutshells without the danger of explosions or fire during grinding.

Thus, a nutshell flour of <325 mesh (mesh size 45 $\mu$m) may be produced from nutshells at a working temperature of the device of up to 275° F. (corresponding to 135° C.) by cooling the mill work with 0.1 to 0.5 gallons (corresponding to 0.4 to 1.9 liters) of water per minute. The residual moisture of this nutshell flour amounts to 2 to 4%.

U.S. Pat. No. 4,279,890 relates to powder compositions which comprise walnut shell flour and have a good absorption of body fluid, in particular to facial powder compositions. The walnut shell flour, the production of which is not explained in greater detail, is used in the form of a powder having a particle size of less than 40 $\mu$m, preferably of less than 30 $\mu$m, which—according to the statements of this state of the art—is a compelling size to recognize its properties as a filler and oil-absorbing agent. The content of the walnut shell flour in the cosmetic compositions amounts to between 30 and 99%, the rest consisting of other oil and/or moisture absorbing fillers, binders, other auxiliary materials and additives.

Japanese patent application No. J 611 59 495 discloses a cleaning composition comprising polysaccharide and ethylene-maleic-anhydride-copolymer; as abrasive agents it includes $SiO_2$, $Al_2O_3$, MgO, SiC, $B_4C$, $Fe_2O_3$, $TiO_2$ and others as well as additives, such as perfume, dyes, fungicial agents, rust inhibitors, bleaches, and pH-controlling agents.

Similar abrasives are described in Japanese patent application No. J 59 036 200.

To exclude the risk of an excessive abrading action of inorganic materials, wood flour has been introduced as abrasive in cosmetic products (Haut und Beruf, Strategien zu berufsbedingten Hauterkrankungen, H. Tronnier, Grosse-Verlag, Berlin 1989, pages 84/85).

However, it has been known for a long time that wood dust may have detrimental effects on the skin and the respiratory system due to components acting as allergens. Examples of wood components injurious to health include resins, terpenes, phenols, tannins, and quinones.

In other products a light wood flour which is free of resin and barks is used, this flour is said to comprise smaller amounts of possible allergenic accompanying substances (Humane Produktion, 7/88, pages 8 and 9, Fair Report on the 9th Trade Exhibition: Arbeitssicherheit [Industrial Safety] in Hannover).

A skin cleansing paste comprising as abrasives light wood flour and granular material of mainly untreated olive kernels is described in an advertisement of Chemische Fabrik Wilden GmbH, P. O. Box 10 11 80, 6078 Neu-Isenburg 1, Germany.

However, wood flour exhibits a high germ content and, as a result of its soft, fibrous structure, swelling processes in the final product occur resulting in an undesired viscosity increase and, as a consequence, in application technological disadvantages. In addition, about 2%-wt. of brightening pigments, e.g., titanium dioxide, have to be added to obtain bright, clean-looking and cosmetically acceptable products.

These disadvantages of wood meal are cleared up, if abrasives based on polyethylene or polyurethane powder are used. However, the shortcoming of plastic powders is the fact that they are not biodegradable and in several instances result in an irregular particle size distribution due to difficult milling processes. Thus—also caused by the low powder density of these materials—problems with respect to formulation technology occur in the production of cosmetic products.

Natural abrasives, such as washed and ground walnut shells, as well as ground apricot stones or olive kernels have been introduced as materials which, based on their hardness and grain size, are suitable for superficial skin cleansing. Although these materials are treated with germicides, the maximum number of organisms amounts to about 200 /g (see, for example, folder of Cosmetochem AG, Riedstraβe 7, CH-6330 Cham, Switzerland).

These materials have a gentle, excellent cleaning action and do not scratch the skin. However, like polyurethane powders, they result in cosmetic products having a dark and dirty appearance. Consequently, in the case of wood flour, brightening pigments, e.g., titanium dioxide, have to be added in an amount of about 2% by weight.

A bleaching process for shells of walnuts is described in Research and Industry, Volume 29, March 1984, pages 10–16.

A treatment with sodium hydrogensulfite and other materials shall improve the appearance of the shells to facilitate the export of the walnuts from India to Europe.

The mentioned state of the art makes it clear that there still is an urgent need for an abrasive that—with the lowest possible concentration or even complete omission of brightening substances—results in optically bright and cosmetically acceptable, clean products when used in cosmetic cleaning agents. It is to be a natural product with a germ content below 100 /g and a minimum of allergenic substances; in addition, it is to be biodegradable and shall exhibit a defined, constant particle size distribution.

SUMMARY OF THE INVENTION

It is the object of the present invention to provide an abrasive for cosmetic products.

This object is achieved by a specially obtained and composed abrasive substance. Thus, the present invention relates to an abrasive for cosmetic preparations, which may optionally comprise surfactants, soaps or other emulsifiers, organic solvents or oils, as well as, optionally, thickeners, builders, re-greasing agents, perfumes, preservatives, dyes and antioxidants, characterized by the fact that it comprises bleached, natural shell and/or kernel flour.

Another object of the present invention is to provide a process for the manufacture of said abrasive characterized in that natural shells and/or kernels are ground into a flour of a defined grain size, the flour is treated with a bleaching agent in hydrous suspension, then filtered off and finally washed with water and dried.

Yet another object of the present invention is to use said abrasive in skin cleaning agents. Still a further object of the present invention is to provide cosmetic preparations, in particular hand washing and hand cleansing agents, comprising the above mentioned abrasive.

The preferred bleaching agent is aqueous hydrogen peroxide solution. According to the present invention the production of the abrasive is characterized by grinding natural shells and/or kernels into a flour of a defined particle size distribution, treating the flour in aqueous suspension with a bleach, followed by filtering it off and washing and drying it.

According to the present invention the abrasive is used, for example, in solventless or solvent-containing hand cleaning pastes, anhydrous skin cleansing agents and peeling creams.

The natural shell and/or kernel flour may, for example, be that of walnut shells, almond shells, hazelnut shells, olive kernels, apricot stones, cherry stones, or other natural shell or kernel flours, e.g., that of palm kernels and coconuts, pistachio nut and pine-nut shells and other pomaceous fruit, as well as any mixture of the named materials.

To obtain a product having the desired particle size distribution, the shell and/or kernel material is ground into a flour in a manner known per se, optionally including screening, the particle size amounting to 50 to 2000 $\mu$m, preferably 70 to 1000 $\mu$m, and in particular 80 to 400 $\mu$m.

The known comminuting machines or mills may be used for grinding, examples thereof include: impact mills with pendulum or plate impact, grind rolling mills, hammer or pinned disk mills, optionally with classifier units, e.g., Condux-mills. In a stirrer vessel the flour is then treated, e.g., with an aqueous solution of hydrogen peroxide used as bleach at a temperature of 20° C. to 100° C., preferably of 50° C. to 100° C. within a period of 300 to 30 minutes, preferably 60 to 90 minutes. The concentration of the hydrogen peroxide amounts to 1.0% by weight to 10.0% by weight, preferably 1.0% by weight to 3.0% by weight, relative to the total initial charge. It is preferred that the bleach, e.g., the hydrogen peroxide, is used in combination with a stabilizer during the bleaching treatment. If the bleaching is effected with hydrogen peroxide, examples of suitable stabilizers include soda water glass, magnesium chloride, carboxylic acids, and phosphoric acids as well as chelating agents and polyacrylic acid and/or the salts thereof.

Residues of $H_2O_2$ may, optionally, be destroyed by reducers, e.g., sodium hydrogensulfite or ascorbic acid, or by increasing the temperature of the suspension to 100° C.

Subsequently, the flour is filtered off and washed with water to remove residues of water-soluble impurities. The product thus obtained is dried at 100° C. to 170° C., preferably at 120° C. to 150° C., or under vacuum within a temperature range of 60° C. to 140° C., up to a residual moisture content of 10% by weight, preferably 0.2 to 8.0% by weight.

The dry product may now be used in different cosmetic preparations. The use in skin cleansing agents, however, is a particularly suitable application.

Surprisingly, bright, clean and cosmetically acceptable pastes may be obtained with such a bleached natural flour, whereby titanium dioxide may completely be omitted or used in an amount of only 0.5%-wt. Whereas—prior to bleaching—the natural flours exhibit germ contents of $10^3$ to $10^4$/g and sometimes even more, the bleaching treatment and drying process result in germ contents of clearly below $10^2$/g. Thus the amount of preservatives necessary in the final product can be minimized so that the risk of an allergisation caused by preservatives is reduced. The content of undesired accompanying substances in the flour is reduced by the bleaching and washing procedure. The bleached flours are completely biodegradable and are present in a defined and constant particle size distribution. Connected with a higher rigidity, as compared to that of the wood flour, the uniform grain size distribution allows to achieve a viscosity which is appropriate for hand cleaning pastes without the occurance of swelling processes.

The examination of bleached walnut shell flour with respect to sensitising effects did not indicate an activation of the immunologic system. Thus, one may not expect that, in case of a human exposure, there will be an allergenic potential after dermal contact.

DESCRIPTION OF THE PREFERRED EMBODIMENTS

The following examples will illustrate the process for the manufacture and the use of the abrasive according to the present invention.

EXAMPLE 1

Bleaching of natural shell or kernel flour with hydrogen peroxide.

The bleaching process is carried out in a 1000-liter-alloy steel apparatus equipped with multistage impulse counter-current agitator, heating and cooling device. The starting preparation amounts to 518.3 kg.

300.0 kg water 150.0 kg walnut shell flour, mean grain size 100–200 $\mu$m 26.3 kg sodium hydroxide solution, 45%

3.0 kg soda water glass and 3.0 kg magnesium chloride are placed in the reactor vessel.

The dark brown suspension is heated to 60° C. under constant stirring. 26.3 kg hydrogen peroxide (35%) are added continuously within a period of 30 minutes. After half of the addition, the suspension changes its color from dark brown to beige. To complete the reaction, stirring is continued for 90 minutes, and the residual hydrogen peroxide content is determined by titration.

In order to reduce the excessive hydrogen peroxide, the equimolar amount of ascorbic acid or sodium sulfite may be added, or the decomposition is achieved by heating to 90° to 100° C.

The suspension is filtered over a chamber filter press, and the filter cake is washed with hot water. Subsequently, the water content amounts to about 50%.

The moist natural flour is then dried in a moving stream dryer up to a residual water content of 5.1%. A disk dryer may also be used.

The yield amounts to about 95%, relative to the flour employed.

In said dry condition, the bleached flour can be stored for several weeks and months without spoiling microbially. It may directly be used in hand cleaning pastes.

EXAMPLE 2

When the technical process had been optimized, the amount of the employed magnesium chloride could be reduced by 50% and that of the used hydrogen peroxide by 21.6%. Thus, in case of an initial charge of 518.3 kg, only 1.5 kg magnesium chloride and only 20.6 kg hydrogen peroxide (35%) are necessary to achieve the same bleaching result.

A further improvement of the bleaching process was achieved by substituting the stabilizers soda water glass and magnesium chloride by phosphoric acid and by carrying out the process at room temperature. The remaining hydrogen peroxide is washed out with the washing water, or it is destroyed during the drying process. The advantages are: saving of process time, energy cost and raw material cost. The portion of hydrogen peroxide needed for the reaction could be reduced once again by 25%, relative to the starting concentration.

Examples 3 to 6 relate to a solventless and a solvent-containing formulation of a hand cleaning paste according to the present invention, a formulation of a solventless hand cleaning paste without $TiO_2$ or with only a small portion of $TiO_2$ and preservative, as well as to an anhydrous skin cleansing agent and a peeling cream with bleached flour of shells and/or kernels.

EXAMPLE 3

Formulation of a solventless hand cleaning paste.

| Raw material | Amount used/ %-wt. |
|---|---|
| surfactant combination consisting of | 18.00 |
| sodium lauryl sulfate and | |
| sodium alkylbenzene sulfonate, 50% | |
| castor oil sulfonate, 68% | 10.00 |
| water | 51.30 |
| citric acid | 0.30 |
| carboxymethylcellulose | 1.00 |
| olein | 2.00 |
| titanium dioxide | 2.00 |
| bleached shell or kernel flour, e.g., walnut shell flour, <350 μm | 15.00 |

-continued

| Raw material | Amount used/ %-wt. |
|---|---|
| hexamethylenetetramine | 0.20 |
| perfume | 0.20 |
| | 100.00 |

EXAMPLE 4

Formulation of a solventless hand cleaning paste with a small proportion of titanium dioxide and preservative.

| Raw material | Amount used/ %-wt. |
|---|---|
| surfactant combination consisting of | 18.00 |
| sodium lauryl sulfate and | |
| sodium alkylbenzene sulfonate, 50% | |
| castor oil sulfonate, 68% | 10.00 |
| water | 52.97 |
| citric acid | 0.30 |
| carboxymethylcellulose | 1.00 |
| olein | 2.00 |
| titanium dioxide | 0.50 |
| bleached shell or kernel flour, e.g., walnut shell flour, <250 μm | 15.00 |
| 2-bromo-2-nitropropane-1,3-diol | 0.03 |
| perfume | 0.20 |
| | 100.00 |

EXAMPLE 5

Formulation of a solventless hand cleaning paste without titanium dioxide portion.

| Raw material | Amount used/ %-wt. |
|---|---|
| surfactant combination consisting of | 18.00 |
| sodium lauryl sulfate and | |
| sodium alkylbenzene sulfonate, 50% | |
| castor oil sulfonate, 68% | 10.00 |
| water | 53.47 |
| citric acid | 0.30 |
| carboxymethylcellulose | 1.00 |
| olein | 2.00 |
| bleached shell or stone flour, e.g., olive kernel flour, <400 μm | 15.00 |
| 2-bromo-2-nitropropane-1,3-diol | 0.03 |
| perfume | 0.20 |
| | 100.00 |

EXAMPLE 6

Formulation of a solvent-containing hand cleaning paste.

| Raw material | Amount used/ %-wt. |
|---|---|
| sodium monoethanolamine fatty alcohol sulfate, 40% | 37.00 |
| castor oil sulfonate, 68% | 14.00 |
| water | 11.97 |
| citric acid | 0.30 |

-continued

| Raw material | Amount used/%-wt. |
|---|---|
| carboxymethylcellulose | 2.00 |
| n-paraffin | 19.00 |
| silicon dioxide | 0.50 |
| bleached shell or kernel flour, e.g., walnut shell flour, <250 μm | 15.00 |
| 2-bromo-2-nitropropane-1,3-diol | 0.03 |
| perfume | 0.20 |
| | 100.00 |

Other surfactants, such as sodium fatty alcohol ether sulfate, cocamidopropyl betaine, alkyl polyglycosides, or admixtures thereof may also be used for formulating the hand cleaning pastes.

The products are manufactured according to the usual and known processes which are commonly known for formulations of surfactant systems (G. Ziolkowski, Kosmetik-Jahrbuch 1986, 1987, 1989, Verlag fur Chemische Industrie, H. Ziolkowski KG Augsburg; W. Umbach, Kosmetik, 1988, Georg-Thieme-Verlag Stuttgart, in particular chapter 5 and 13).

EXAMPLE 7

Formulation of an anhydrous skin cleansing agent.

| Raw material | Amount used/%-wt. |
|---|---|
| fatty alcohol $C_{12}$—$C_{18}$ 5 EO (washing active substances) | 15.0 |
| dimethyl adipate (solvent) | 9.3 |
| dimethyl glutarate (solvent) | 35.3 |
| dimethyl succinate (solvent) | 9.4 |
| isooctyl stearate (re-greasing agent) | 5.0 |
| fumed silica (thickener) | 2.3 |
| ethyleneglycol distearate (thickener) | 7.0 |
| cellulose acetate butyrate (thickener) | 3.8 |
| perfume | 0.4 |
| walnut shell flour, <250 μm, bleached | 12.5 |
| | 100.0 |

EXAMPLE 8

Formulation of a peeling cream.

| | | Amount used/%-wt. |
|---|---|---|
| A. | MIGLYOL[R] 812 neutral oil (mixed acidic triglyceride of fract. C8–10 coconut fatty acids; manufacturer: Dynamit Nobel AG) | 66.45% |
| | IMWITOR[R] 780 K (manuf.: Dynamit Nobel AG) | 5.0% |
| | Teginacid[R] (mixture of glycerol mono-distearates with portions of poly(ethylene glycol) fatty alcohol ethers; manufacturer: TH.Goldschmidt AG) | 3.4% |
| | Texapon[R] L 100 (sodium lauryl sulfate manufacturer: Henkel KG aA) | 1.45% |
| | paraffinic oil | 2.5% |
| | phenonip (phenoxyethanol with parabenes, Nipa Laboratories, GB) | 1.0% |
| B. | potato starch | 5.0% |
| | olive kernel flour <300 μm, bleached | 6.0% |
| C. | Aerosil[R] 200 (pyrolytically manufactured highly disperse silicon dioxide, manufacturer: Degussa AG) | 4.0% |
| | Syloid[R] 244 (highly disperse silicic acid; manufacturer: Grace and Co.) | 6.0% |
| | perfume oil | 0.2% |
| | | 100.00% |

EXAMPLE 9

Preservative test with a formulation of a solventless hand cleaning paste.

| Raw material | Amount used/%-wt. |
|---|---|
| surfactant combination consisting of Na-lauryl ether sulfate, cocamidopropyl betaine and castor oil sulfonate, (40%) | 57.9 |
| bleached or unbleached mixture of walnut shells and olive kernel flour, 50:50, <300 μm | 15.0 |
| thickener combination of carboxymethylcellulose and bentonite | 5.0 |
| titanium dioxide | 0.5 |
| citric acid | 0.2 |
| perfume | 0.2 |
| preservative acc. to Table | |
| water | ad 100.0 |

TABLE

| | | | |
|---|---|---|---|
| concentration of the preservative (Bronopol 2-bromo-2-nitropropane-1,3-diol) | 0.00% | 0.03% | 0.08% |
| germs/g when the unbleached mixture was used (after 2 days) | 13,000 (growth) | 2,400 (growth) | 200 (growth) |
| germs/g when the bleached mixture was used (after 2 days) | <100 | <100 | <100 |

When the unbleached shell/kernel-flour-mixture was used in a solventless hand cleaning paste without preservative according to the formulation of Example 9, bacterial counts of $1.3 \times 10^4$ /g were found in the product after 2 days, whereas the product did not exhibit an increased bacterial count when the bleached flour had been used.

There has thus been shown and described a novel abrasive in cosmetic products which fulfills all the objects and advantages sought therefor. Many changes, modifications, variations and other uses and applications of the subject invention will, however, become apparent to those skilled in the art after considering this specification and the accompanying drawing which discloses the preferred embodiments thereof. All such changes, modifications, variations and other uses and applications which do not depart from the spirit and scope of the invention are deemed to be covered by the invention, which is to be limited only by the claims which follow.

We claim:

1. An abrasive for use in a skin cleansing agent comprising a bleached flour obtained from a natural shell, kernel or mixture thereof, the flour having a particle size from 50 to 2000 μm and having been bleached with a 1 to 10% aqueous solution of hydrogen peroxide, and the natural shell, kernel or mixture thereof being selected from the group consisting of walnut shells, almond shells, hazelnut shells, olive kernels, cherry kernels, apricot kernels, and mixtures thereof.

2. A process for preparing an abrasive according to claim 1, which comprises grinding a natural shell, kernel or mixture thereof into a flour having a particle size from 50 to 2000 µm, bleaching the flour with a 1 to 10% aqueous solution of hydrogen peroxide, subsequently filtering off the bleached flour, washing the bleached flour with water and drying, and the natural shell, kernel or mixture thereof being selected from the group consisting of walnut shells, almond shells, hazelnut shells, olive kernels, cherry kernels, apricot kernels, and mixtures thereof.

3. A skin cleansing agent comprising a surfactant, soap or other emulsifier, optionally at least one member selected from the group consisting of organic solvents or oils, thickeners, builders, greasing agents, perfumes, preservatives, dyes and antioxidants, and an abrasive according to claim 1, wherein said abrasive comprises by weight 3 to 95% of the total weight of said skin cleansing agent.

4. An abrasive according to claim 1, wherein the particle size of the flour is from 70 to 1000 µm.

5. An abrasive according to claim 1, wherein the particle size of the flour is from 80 to 400 µm.

6. A process according to claim 2, wherein the bleaching with hydrogen peroxide is in the presence of a stabilizer.

7. A process according to claim 2, wherein the flour has a particle size of 70 to 1000 µm.

8. A process according to claim 2, wherein the flour has a particle size of 80 to 400 µm.

9. A process according to claim 2, wherein the bleaching with hydrogen peroxide is effected at a temperature of 20° C. to 100° C.

10. A process according to claim 2, wherein the bleaching with hydrogen peroxide is effected at a temperature of 50° C. to 100° C.

11. A process according to claim 2, wherein the bleaching with hydrogen peroxide is effected at a temperature of 20° C. to 50° C.

12. A process according to claim 2, wherein the concentration of hydrogen peroxide is from 1 to 3 percent by weight.

13. A process according to claim 2, wherein the treatment with hydrogen peroxide is effected for 300 to 30 minutes.

14. A process according to claim 2, wherein the treatment with hydrogen peroxide is effected for 60 to 30 minutes.

15. A process according to claim 2, wherein the bleached and washed material is dried at 100° C. to 170° C.

16. A process according to claim 2, wherein the bleached and washed flour is dried at 120° C. to 150° C.

17. A process according to claim 2, wherein the bleached and washed flour is dried under vacuum at a temperature from 60° C. to 140° C.

18. A process according to claim 2, wherein drying is effected to a residual moisture content of at most 10 percent by weight.

19. A process according to claim 2, wherein drying is effected to a residual moisture content of at most 8 percent by weight.

20. A skin cleansing agent according to claim 3, wherein the abrasive is present in from 5 to 70% by weight.

21. A skin cleansing agent according to claim 3, wherein the abrasive is present in from 7 to 50% by weight.

22. A skin cleansing agent according to claim 3, which is a hand cleansing agent.

23. An abrasive according to claim 1, wherein the flour comprises at least one member selected from the group consisting of walnut shells and olive kernels.

24. An abrasive for use in a skin cleansing agent which comprises at least one surfactant, soap or other emulsifier and optionally at least one member selected from the group consisting of organic solvents or oils, thickeners, builders, greasing agents, perfumes, preservatives, dyes and antioxidants, comprising a bleached flour obtained from olive kernels, the flour having a particle size from 50 to 2000 µm and having been bleached with a 1 to 10% aqueous solution of hydrogen peroxide.

25. A process according to claim 2, wherein the flour is ground from a mixture of walnut shells and olive kernels.

26. A process according to claim 2, wherein the flour is ground from at least one of walnut shells, olive kernels, cherry kernels and apricot kernels.

\* \* \* \* \*